US 8,419,184 B1

(12) United States Patent
Butler et al.

(10) Patent No.: US 8,419,184 B1
(45) Date of Patent: *Apr. 16, 2013

(54) OPHTHALMIC EXAMINATION SYSTEM INTERFACE DEVICE

(75) Inventors: Kevin A. Butler, Downers Grove, IL (US); Michael C. Whittenburg, Chicago, IL (US)

(73) Assignee: M+S Technologies, Inc., Skokie, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/481,230

(22) Filed: Jun. 9, 2009

Related U.S. Application Data

(60) Provisional application No. 61/060,241, filed on Jun. 10, 2008.

(51) Int. Cl.
*A61B 3/10* (2006.01)
*A61B 3/00* (2006.01)

(52) U.S. Cl.
USPC ............ 351/205; 351/211; 351/221; 351/246

(58) Field of Classification Search .................. 351/239, 351/246, 205, 211, 221–223, 200, 210, 237, 351/241
See application file for complete search history.

(56) References Cited

U.S. PATENT DOCUMENTS

| 4,803,312 | A | 2/1989 | Britos |
| 5,249,121 | A | 9/1993 | Baum et al. |
| 5,530,493 | A | 6/1996 | Suzuki |
| 5,914,772 | A * | 6/1999 | Dyer ............................. 351/246 |
| 6,731,683 | B1 | 5/2004 | Fiedler et al. |
| 6,761,454 | B2 | 7/2004 | Lai et al. |
| 6,976,216 | B1 | 12/2005 | Peskin et al. |
| 7,364,297 | B2 | 4/2008 | Goldfain et al. |
| 2002/0059257 | A1 | 5/2002 | Matsumura et al. |
| 2005/0036109 | A1* | 2/2005 | Blum et al. ................... 351/168 |
| 2005/0200808 | A1* | 9/2005 | Wyatt ............................ 351/246 |
| 2008/0187033 | A1 | 8/2008 | Smith |
| 2009/0241042 | A1 | 9/2009 | Nordstrom |
| 2010/0265462 | A1 | 10/2010 | Nordstrom |

FOREIGN PATENT DOCUMENTS

WO   WO 2008/150476   12/2008

* cited by examiner

*Primary Examiner* — Dawayne A Pinkney
(74) *Attorney, Agent, or Firm* — Fay Sharpe LLP

(57) ABSTRACT

An automated ophthalmic system is disclosed that is utilized to examine the eyes of a subject. A refraction system measures a refractive error of each eye and identifies a lens to correct the refractive error detected. A display presents one or more of an optotype, a chart, a test and a function to the subject to ascertain the refractive error. An interface device receives a voltage signal from the refraction system, converts the voltage signal into one or more ASCII characters, and communicates the one or more ASCII characters to the display to present the one or more of an optotype, a chart, a test and a function.

20 Claims, 5 Drawing Sheets

OPHTHALMIC EXAMINATION SYSTEM INTERFACE DEVICE

This application claims the benefit of U.S. application Ser. No. 61/060,241, filed Jun. 10, 2008, the disclosure of which is incorporated herein by reference.

BACKGROUND

The present exemplary embodiments relate generally to ophthalmic examination systems. In one particular application, an interface device is utilized to facilitate communication between a refraction system and a display within the ophthalmic examination system. However, it is to be appreciated that the present exemplary embodiment is also amenable to other like applications.

An eye examination is a battery of tests performed by an optometrist or ophthalmologist to assess a subject's vision and ability to focus on and discern objects. An automated ophthalmic exam system can be employed to aid in the determination of a subject's refractive error and to identify an appropriate lens prescription to correct such error. In one example, an automated ophthalmic system includes a phoroptor and an eye chart. The phoroptor is used to present powered lenses in front of a subject's eyes. The eye chart can be read by the subject via the phoroptor to aid in the determination of visual acuity during the test.

The phoroptor can be employed to refine the prescription, identified via the autorefractor, to one which provides the subject with the best vision. The lenses within a phoroptor refract light in order to focus images on the subject's retina. By changing these lenses, the examiner is able to determine the spherical power, cylindrical power, and/or cylindrical axis necessary to correct a subject's refractive error. From the measurements taken, a corrective lens prescription can be identified that contains at least six numerical specifications (three for each eye): sphere, cylinder and axis.

An eye chart is used to measure visual acuity when viewed by the subject via the phoroptor. Types of eye charts can include a Snellen chart, a tumbling E chart, and a Landolt C chart. Charts usually display several rows, wherein each row contains different sized test symbols or optotypes. The subject is asked to identify the optotypes on the chart, usually starting with large rows and continuing to smaller rows until the optotypes cannot be reliably identified any longer. Charts can be employed with very young children or illiterate adults that are incapable of letter recognition. One version uses simple pictures or patterns (e.g., an apple, a house, a square, and a circle) that are selected based upon the results of recognition trials. The tumbling E chart has the block letter "E" turned in different orientations, wherein the subject simply indicates which direction each "E" is facing. Similarly, the Landolt C chart has rows of circles with different segments missing and the subject describes where each broken piece is located.

Eye charts can be presented via a computer-based display and/or a chart projector in concert with the refraction system. There are several potential advantages such as more precise measurement and less examiner induced bias in the examination. Compatibility issues can arise, however, when communication is attempted between a refraction system and a computer-based eye chart produced by disparate manufacturers. In particular, automated ophthalmic exam systems generally employ proprietary protocols to communicate between such components. Accordingly, systems and methods are needed to facilitate communication between automated ophthalmic exam system components, regardless of the manufacturer.

BRIEF SUMMARY OF THE INVENTION

In one aspect, an automated ophthalmic system is utilized to examine the eyes of a subject. A refraction system measures a refractive error of each eye and identifies a lens to correct the refractive error detected. A display presents one or more of an optotype, a chart, a test and a function to the subject to ascertain the refractive error. An interface device receives a voltage signal from the refraction system, converts the voltage signal into one or more ASCII characters, and communicates the one or more ASCII characters to the display to present the one or more of an optotype, a chart, a test and a function.

In another aspect, a method is employed to facilitate communication between a refraction system and a display within an automated ophthalmic system. An interface device is connected between the refraction system and the display. A communication is sent from the refraction system to the interface device. If a predefined voltage change is received within the communication, the voltage change is validated and a response is sent to the refraction system. The predefined voltage change is converted to an ASCII character and sent to the display.

In yet another aspect, an interface device is utilized to communicate data between a refraction system and a display within an automated ophthalmic system. A first data port receives a voltage signal from the refraction system. A second data port facilitates communication between the display and the interface device. A voltage detector detects a predefined voltage change from the voltage signal received by the first data port. An ASCII converter associates one or more ASCII characters with the voltage change detected by the voltage detector. An I/O controller communicates the one or more ASCII characters from the interface device to the display via the second data port.

DETAILED DESCRIPTION

Figure 1:
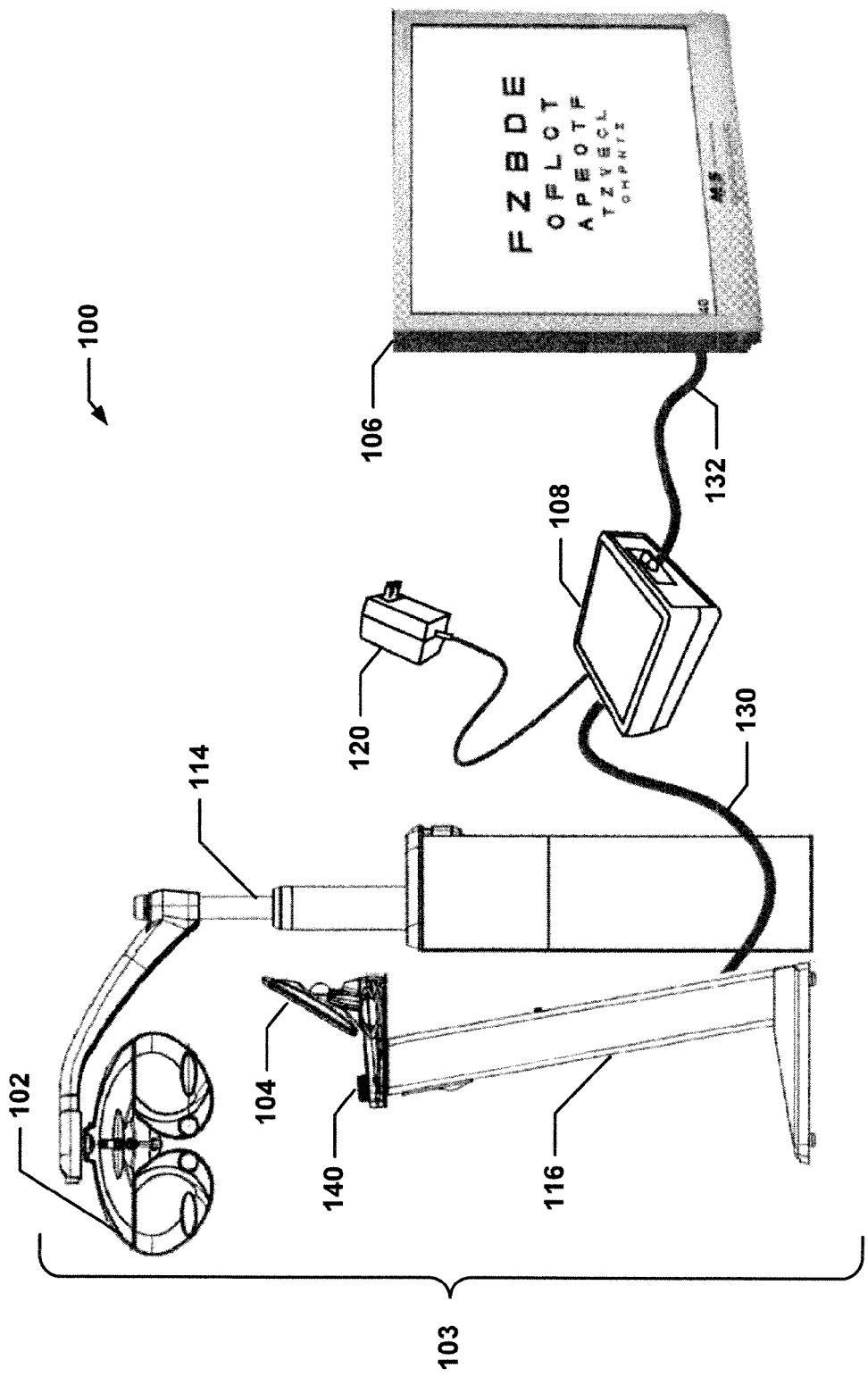
FIG. 1 illustrates an automated ophthalmic exam system, in accordance with an exemplary embodiment.

FIG. 1 illustrates an automated ophthalmic examination system 100 that is utilized to perform eye examinations on subjects. A phoroptor 102 is operated via a user interface 104 to measure a subject's refractive error and to determine an appropriate corrective lens for compensation thereof. The phoroptor 102 and the user interface 104 comprise a refraction system 103 that evaluates vision by presentation of images, such as via a display 106, as viewed by the subject through a plurality of disparate lenses. The user interface 104 is coupled to the display component 106 via an interface device 108. The refraction system 103 can connect to the interface device 108 via a cable 130. The interface device 108 can connect to the display 106 via a cable 132.

Substantially any design, such as coaxial, twisted pair, etc., is contemplated for the cables 130 and 132. Further, substantially any pin configuration and/or connector such as an RJ45 connector, a 7-pin DIN connector, a USB connector, a DB9 connector, a DB25 connector, etc. can be employed to couple the refraction system 103, the interface device 108, and the display 106 to the cables 130 and 132. In one embodiment, the cable 130 utilizes a 7-pin DIN connector and the cable 132 uses an RJ-45 connector. In addition, any protocol or standard can be utilized to communicate via the cables 130 and 132 such as RS-232, RS-485, Ethernet, etc. to facilitate communication therebetween. The interface device 108 can receive power from an external source via a power adaptor 120. In one example, the power adaptor 120 transforms 110 volts AC from a wall outlet to a 9-volt DC power source for consumption by one or more components within the interface device 108.

The phoroptor 102 can provide automated functionality to facilitate intuitive operator usage. In one aspect, a dial 140 can allow an operator to quickly change sphere, cylinder and axis powers with one hand to provide a reliable examination. The user interface 104 can present data to a user via a touch screen (e.g., a TFT LCD) and can include one or more slots for data transfer via a card, stick jump drive or equivalent memory device. The user interface 104 can provide operation and question guidance to an operator within an examination proceeding. In this manner, inexperienced operators can provide accurate and reliable ophthalmic examinations by following instructions provided on the user interface 104. The user interface 104 can present near vision charts and/or program/operation messages to facilitate selection of one or more examination protocols and/or specific eye charts can for presentation via the display 106.

An arm 114 can support the phoroptor 102 to allow articulation along a rotational and/or a vertical axis to accommodate a plurality of subject sizes. A stand 116 can be utilized to support the user interface 104 for convenient operator access when performing ophthalmic examinations. In one embodiment, the stand can contain a processing module (not shown) to facilitate communication between the refraction system 103 and the interface device 108. Alternatively or in addition, the stand 116 can contain one or more ports to connect disparate peripheral devices to the refraction system 103. Such peripheral devices can include a mouse, a pointer, a roller ball, a printer, and/or a plotter, for example. In one embodiment, the peripheral device is an autorefractor and/or a lensometer. Such devices can provide an objective measurement of a subject's refractive error and prescription for corrective lenses by examining the subject's eyes and/or corrective lenses respectively.

The display 106 can include a processor to provide processing support for the execution of the transfer and processing of the voltage signals and/or ASCII characters. It is to be appreciated that although a standalone architecture is illustrated, that any suitable computing environment can be employed in accordance with the present embodiments. For example, computing architectures including, but not limited to, stand alone, multiprocessor, distributed, client/server, minicomputer, mainframe, supercomputer, digital and analog can be employed in accordance with the present embodiment.

The processor can include a processing unit (not shown), a system memory (not shown), and a system bus (not shown) that couples various system components including the system memory to the processing unit. The processing unit can be any of various commercially available processors. Dual microprocessors and other multi-processor architectures also can be used as the processing unit. The system bus can be any of several types of bus structure including a memory bus or memory controller, a peripheral bus, and a local bus using any of a variety of commercially available bus architectures. The memory includes read only memory (ROM) and random access memory (RAM). A basic input/output system (BIOS), containing the basic routines that help to transfer information between elements within the computer, such as during start-up, is stored in ROM.

The processor can further include a hard disk drive, a magnetic disk drive, e.g., to read from or write to a removable disk, and an optical disk drive, e.g., for reading a CD-ROM disk or to read from or write to other optical media. The processor typically includes at least some form of computer readable media. Computer readable media can be any available media that can be accessed by the processor. By way of example, and not limitation, computer readable media may comprise storage media and communication media. Storage media includes volatile and nonvolatile, removable and non-removable media implemented in any method or technology for storage of information such as computer readable instructions, data structures, program modules or other data. Storage media includes, but is not limited to, RAM, ROM, EEPROM, flash memory or other memory technology, CD-ROM, digital versatile disks (DVD) or other magnetic storage devices, or any other medium which can be used to store the desired information and which can be accessed by the processor.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above can also be included within the scope of computer readable media.

A number of program modules may be stored in the drives and RAM, including an operating system, one or more application programs, other program modules, and program non-interrupt data. The operating system in the processor can be any of a number of commercially available operating systems.

A user may enter commands and information into the processor through a keyboard (not shown) and a pointing device (not shown), such as a mouse. Other input devices (not shown) may include a microphone, an IR remote control, a joystick, a game pad, a satellite dish, a scanner, or the like. These and other input devices are often connected to the processing unit through a serial port interface (not shown) that is coupled to the system bus, but may be connected by other interfaces, such as a parallel port, a game port, a universal serial bus ("USB"), an IR interface, etc.

Further, the display 106 can include a monitor or similar unit to present images. The monitor (or other type of display device) is also connected to the system bus via an interface, such as a video adapter (not shown). In addition to the monitor, a processor typically includes other peripheral output devices (not shown), such as speakers, printers etc. The monitor can be employed with the processor to present data that is electronically received from one or more disparate sources.

For example, the monitor can be an LCD, plasma, CRT, etc. type that presents data electronically. Alternatively or in addition, the monitor can display received data in a hard copy format such as a printer, facsimile, plotter etc. The monitor can present data in any color and can receive data from the processor via any wireless or hard wire protocol and/or standard.

The processor can operate in a networked environment using logical and/or physical connections to one or more remote computers, such as a remote computer(s). The remote computer(s) can be a workstation, a server computer, a router, a personal computer, microprocessor based entertainment appliance, a peer device or other common network node, and typically includes many or all of the elements described relative to the processor. The logical connections depicted include a local area network (LAN) and a wide area network (WAN). Such networking environments are commonplace in offices, enterprise-wide computer networks, intranets and the Internet.

When used in a LAN networking environment, the processor is connected to the local network through a network interface or adapter. When used in a WAN networking environment, the processor typically includes a modem, or is connected to a communications server on the LAN, or has other means for establishing communications over the WAN, such as the Internet. In a networked environment, program modules depicted relative to the processor, or portions thereof, may be stored in the remote memory storage device. It will be appreciated that network connections described herein are exemplary and other means of establishing a communications link between the processors may be used.

The display 106 can present images to be viewed by the subject for acuity testing. In one example, letters, numbers, lines, pictograms, dots, tumbling Es, Landolt Cs, and/or ETDRS charts can be selected. Such optotypes can be presented in a plurality of sizes according to disparate testing configuration protocols. Alternatively or in addition, contrast sensitivity can be measured by presenting optotypes in a plurality of darkness levels. The display can be a backlit flat screen device such as an LCD or plasma monitor. Additional tests such as red-green and red-blue anaglyph stereo testing can also be presented via the display 106 for use with appropriate glasses. In one embodiment, the display 106 can be mounted to a wall or other vertical surface to provide height appropriate chart presentations. A wireless hand-held controller (not shown) can be utilized to replace or supplement the functionality of the refraction system 103 (e.g., to select one or more tests, optotype sizes, fixation, etc.).

The interface device 108 is utilized to emulate a chart projector or proprietary computer display that is typically used with the refraction system 103. In this manner, the refraction system 103 can operate a non-projector device, such as the display 106, via equivalent commands to present desired images to an exam subject. Thus, the interface device 108 eliminates the need to modify/replace the communication protocol of the refraction system 103 and allows communication with any models associated with the display 106 for presentation of images thereof. In one example, the interface device 108 includes a processing component that identifies communication changes from both the refraction system 103 and the display 106.

In one example, the interface device 108 is coupled to the refraction system 103 via a 7-pin DIN connection and the display 106 via a serial connection. When a predefined voltage change or wave pattern is detected by the interface device 108 (e.g., from the refraction system 103), the interface device validates the voltage change and sends a response to the refraction system 103. The defined voltage change is converted by the interface device 108 to an ASCII character, which is sent to the display via the communication cable 132. In one embodiment, the voltage change is associated with the ASCII character via a lookup table.

Thus, the display 106 does not directly read voltage changes sent from the refraction system 103. Instead, the ASCII characters are received from the interface device 108 to provide greater isolation and error handling throughout the automated ophthalmic exam system 100. In another example, the interface device 108 is utilized to convert a first protocol from the refraction system 103 to a second protocol that for communication to the display 106. In an exemplary embodiment, the cable 130 communicates via a binary electrical standard and the cable 132 communicates via an RS-232 standard.

The interface device 108 can include three connections: (1) a seven pin DIN connector to couple the interface device 108 to the refraction system 103 via the communication cable 130, (2) an RJ-45 connector to couple the display 106 to the interface device 108 wherein the display 106 has an RS-232 port that is connected to the RJ-45 connector via a DB-9 to RJ-45 adapter, and (3) a 2.1 millimeter barrel connector for connection to the power adaptor 120 that provides a predetermined DC voltage. The interface device can utilize a flash microcontroller, such as a Microchip Technology Model 18F1320 with 8K of flash memory stored on an interface program.

The interface device 108 can communicate with the refraction system 103 via opto-isolators to provide galvanic isolation between the refraction system 103 and the interface device 108. In one example, the interface device 108 communicates with the display 106 via an RS-232 protocol at 9600 baud, no parity, 1 stop bit, wherein no flow control is utilized. It is to be appreciated that a plurality of disparate connectors and support for multiple communication standards is contemplated to facilitate connection of substantially any model refraction system with substantially any model display. Further, the interface device 108 can transmit and/or receive data to/from one or more disparate components via a wireless signal, such as Bluetooth or infrared for example. In such cases, a wireless transponder (not shown) can be employed.

Figure 2:
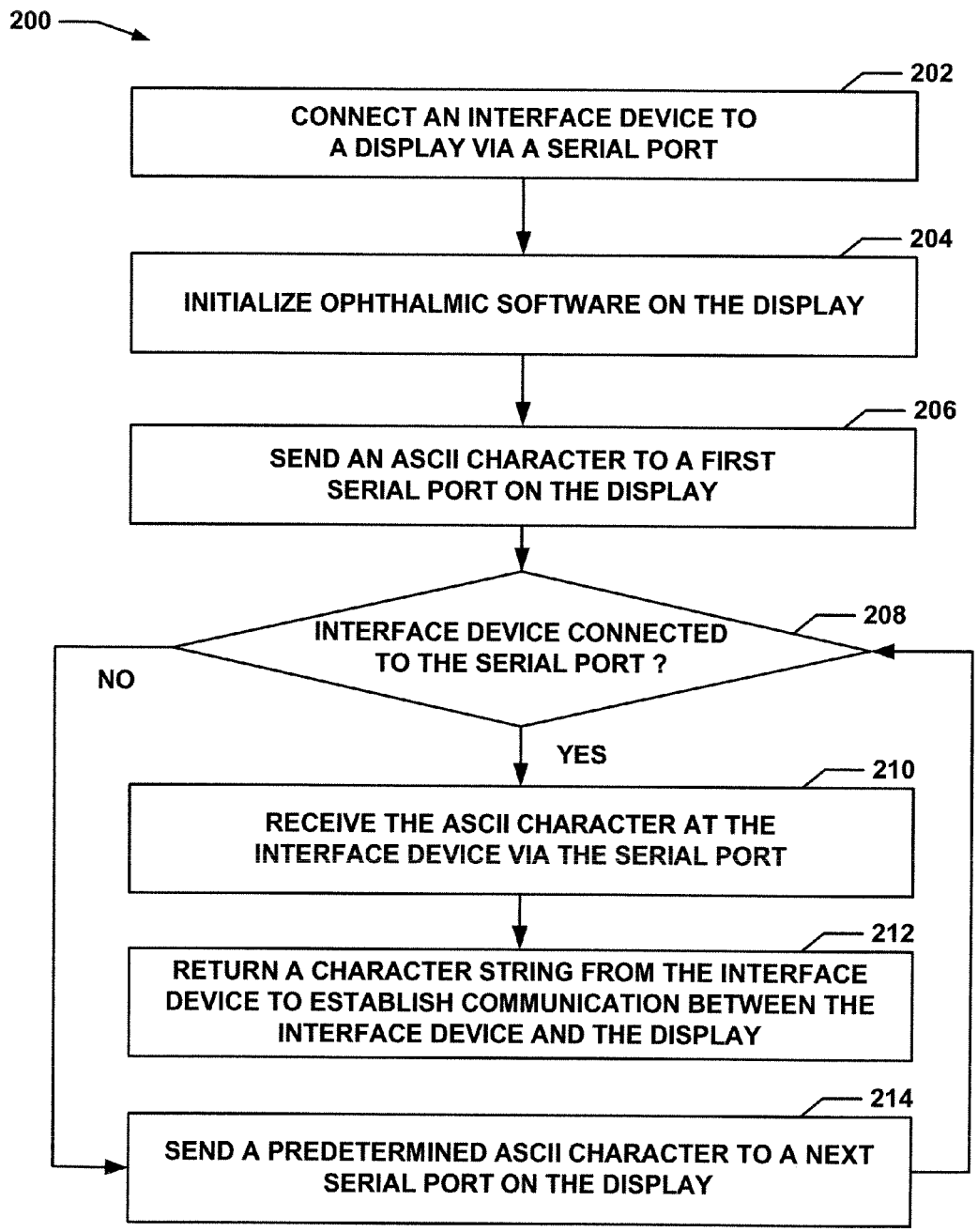
FIG. 2 illustrates a method to establish communication between an interface device and a display within the automated ophthalmic exam system, in accordance with an exemplary embodiment.

FIG. 2 illustrates a method to establish communication between an interface device (e.g., 108) and a display (e.g., 106). At reference numeral 202, an interface device is connected to a display via a serial port. At 204, ophthalmic software is initialized on the display and, at 206, an ASCII character is sent to a first serial port residing on the display. At 208, a determination is made whether an interface device is connected to the serial port through which the ASCII character was sent. If so, at 210, the ASCII character is received at the interface device via the serial port.

At 212, a character string is returned from the interface device to establish communication between the interface device and the display. In one example, the character string is five characters in length. Thus, when the display receives the character string message, it verifies that a particular serial port is connected to the interface device. If the interface device is not connected to the serial port through which the ASCII character was originally sent, at 214, a predetermined ASCII character is sent to a next serial port on the display. If an ASCII character is sent to every serial port on the display and does not receive a return character string, an error is displayed. In this manner, the interface device can be automatically discovered, regardless of the serial port it is connected to on the display.

Figure 3:
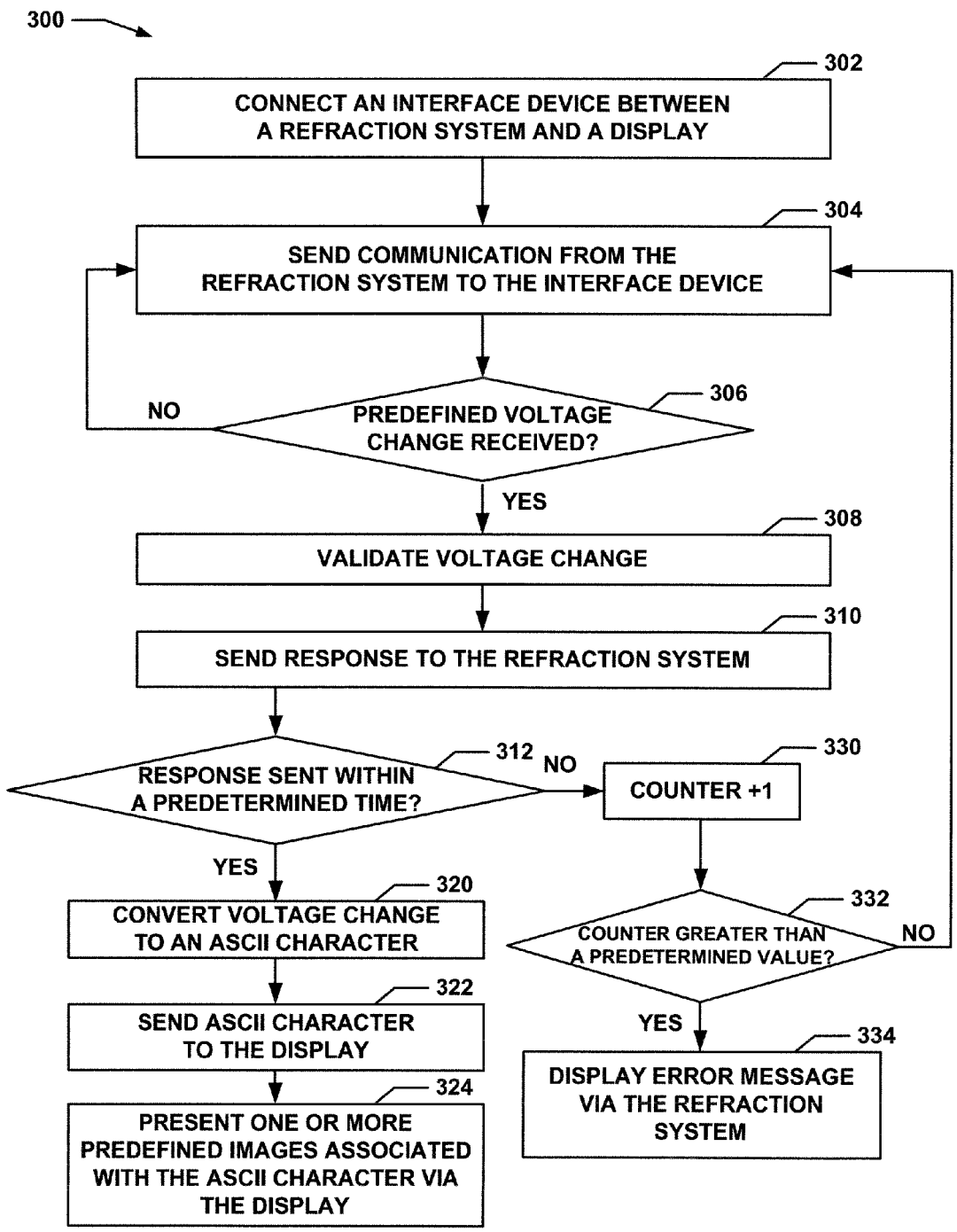
FIG. 3 illustrates a method to present an image from a refraction system to the display via an interface device, in accordance with an exemplary embodiment.

FIG. 3 illustrates a method to present one or more predefined images via a display. At 302, an interface device is connected between a refraction system and the display. At 304, communication is sent from the refraction system to the interface device. If a predefined voltage change is received at 306, the voltage change is validated at 308 and a response is sent to the refraction system at 310. If, however, the predefined voltage change is not received, the method returns to reference numeral 304 to send communication again from the refraction system to the interface device.

Once the response is sent to the refraction system at 310, a verification is made at 312 to determine that the response was sent within a predetermined window of time. If so, the voltage change is converted to one or more ASCII characters at 320. The conversion of the voltage change to one or more ASCII characters can come from a predefined configuration, such as a look up table and/or memory store. At 322, the one or more ASCII characters are sent to the display and presented and associated with one or more predefined images to be presented via the display at 324. In this manner the voltage change received by an interface device can be correlated to one or more ASCII characters for consumption via the display.

In turn, the one or more ASCII characters can be associated by the display to one or more images for presentation to a subject receiving an optical exam. If the response to the refraction system is not set within a predetermined time, at 312, a counter is incremented at 330 and an error message is displayed at 334 if the counter is greater than a predetermined value at 332. If, however, the counter is not greater than a predetermined value, communication is once again sent from the refraction system to the interface device at 304 to reset the method. After the response is sent to the refraction system (via an ACK or equivalent), an RS-232 string can be sent to the display. Such message can be transmitted in a standard RS-232 format (e.g. 9600 baud, 8 bits, no parity with one stop bit) and can consist of a hexadecimal representation of the information sent by the display in a proprietary format.

The display receives this message and changes the displayed chart as needed. The display, however, does not need to acknowledge the messages that are sent by the interface device. In one embodiment, the only time the display transmits to the interface device is during initialization when it sends an ASCII character command to locate the interface device. Once this configuration is complete and the use of the interface device is selected, the user will have no further steps. The interface device and display are prepared to communicate and work together anytime the systems are turned on. Thus, when an operator presses a button on the refraction system, the appropriate chart will be shown in the display via the interface device. In addition, an operator can have the ability to simultaneously operate the display via a serial remote/infrared or other input device. Such functionality allows the operator to utilize the various charts and functionality that may not be available via the refraction system.

Figure 4:
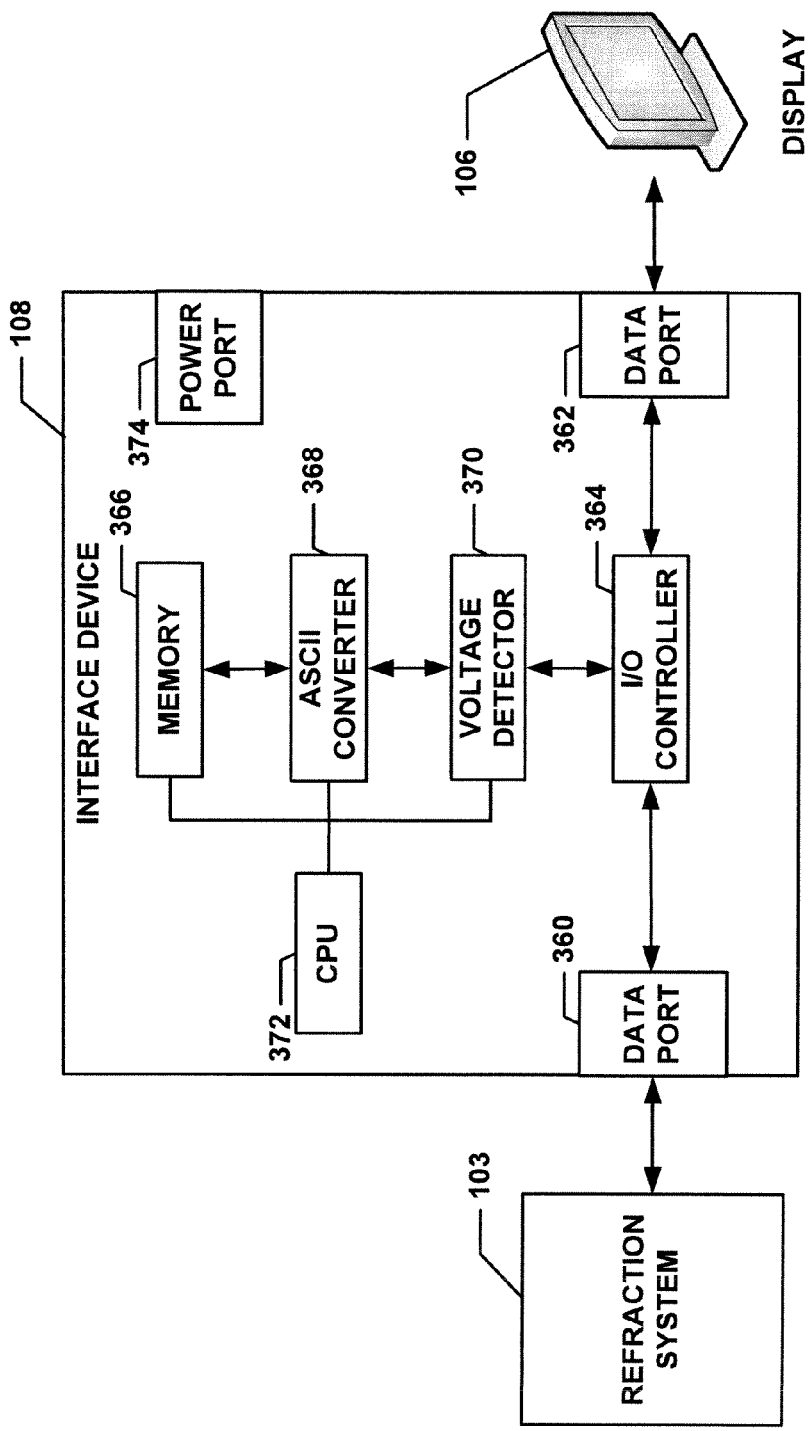
FIG. 4 illustrates an exemplary embodiment of the interface device, in accordance with an exemplary embodiment.

FIG. 4 illustrates the components within the interface device 108. Voltage signals are received from the refraction system 103 by the interface device 108 via a data port 360. In one embodiment, the data port 360 is a serial DIN port although substantially any port configuration is contemplated. Voltage signals received by the data port 360 can be communicated to a data port 362 and on to the display 106 via an I/O controller 364. The data port 362, in one embodiment, is a serial port that facilitates communication of ASCII strings via a particular protocol such as RS-232. The I/O controller 364 is utilized to govern the flow of data between the data ports 360 and 362 and on to the refraction system 103 and the display 106. A power port 374 delivers power from an external source to the interface device 108.

Voltage signals received via the data port 360 are communicated to a voltage detector 370 to determine if a predefined change in the voltage signal has been received. The voltage changes can be reflective of disparate digital values (e.g., 1 and j), wherein the 1 or 0 can be associated with a predetermined voltage and associated with a HIGH and a LO value respectively. The values can have a predetermined time duration for either voltage level and/or a predetermined sequence of voltage levels. In this manner, the variation in voltage level within a predetermined message string location can be interpreted and processed via the interface device 108.

If a predefined voltage change is detected, an ASCII converter 368 is utilized to convert the change in the voltage signal into one or more ASCII characters for communication via the data port 362. In one embodiment, the conversion can include an intermediate step wherein one or more hexadecimal values are first associated with the voltage signal, wherein the hexadecimal value is associated with one or more ASCII characters for transmission to the display 106. A memory store 366 can be utilized by the ASCII converter 368 to obtain a table of associated voltage change values with ASCII characters. In one example, the memory store 366 contains one or more look up tables that contain information to allow the storage, editing and retrieval of such information. The ASCII characters can be related to images presented and/or a function of the display 106 such as an optotype, a chart, a test, a function, a positive image of the display, a negative image of the display, a contrast of images presented on the display, and a color of the display.

A CPU 372 is utilized to provide processing support for the execution of the transfer and processing of the voltage signals and/or ASCII characters within the interface device 108. The CPU 372 can be employed to support the systems and methods herein including the refraction system 103, the display 106, the interface device 208 and the methods 200 and 300. The CPU 372 can include the same or similar functionality as described with regard to the processor within the display 106, described above.

In one example, the CPU 372 executes exemplary pseudo code to facilitate functionality of the interface device 108, as outlined below.

1. The code begins by initializing the hardware, then calling the main( ) function.
2. The main( ) function contains a infinite "while" loop which first calls the time_low( ) function.
    1. The time_low( ) function waits for the input pin from the refraction system 103 to go low. At the same time, it repeatedly checks for any RS-232 input from the display 106. If the time_low( ) receives a predetermined ASCII character, the function sends back a predetermined character string for identification. Otherwise, the character is ignored.
    2. While time_low( ) is waiting for input pin from the refraction system to go low, or for RS-232 input, the system periodically blinks an "activity" LED so that an operator can see the system is working.
    3. If time_low( ) sees the input pin from the refraction system going low, it resets the timer0 and then waits for the refraction system input pin to go back high. Once it does, it checks the new value of timer0 to get the overall time that the input pin was low. This value is returned to the calling function.
3. The main( ) function then checks to see if the returned value (the time the input pin was low) is between 7.9 and 8.9 msec. If it is within range, the system proceeds to try to receive a valid message from the refraction system 103. Otherwise, the system assumes something isn't right, and goes back to the beginning of the infinite "while" loop.

4. The main( ) function then calls the time_high( ) function to time the amount of time the input from the refraction system 103 is high. If the returned value is between 3.7 and 4.4 msec, then the system proceeds to try to receive a valid message from the refraction system 103. Otherwise, the system assumes something isn't right (error), and goes back to the "while" loop.

5. Next, the main( ) function calls the receive_byte( ) and receive_byte3( ) functions to read the incoming data bits from the refraction system 103 and converts them into a series of three bytes.

6. If no error was detected in the reception of these bytes, then the system sends the received bytes to the display 106 via the RS-232 port in hexadecimal format. It then sends an acknowledgement back to the refraction system 103. If an error is detected, the system doesn't send anything back to the refraction system 103, which causes the refraction system 103 to timeout and resend the message.

7. Finally, the system goes back to the beginning of the infinite while loop, where it calls time_low( ) again to start the process all over.

Figure 5:
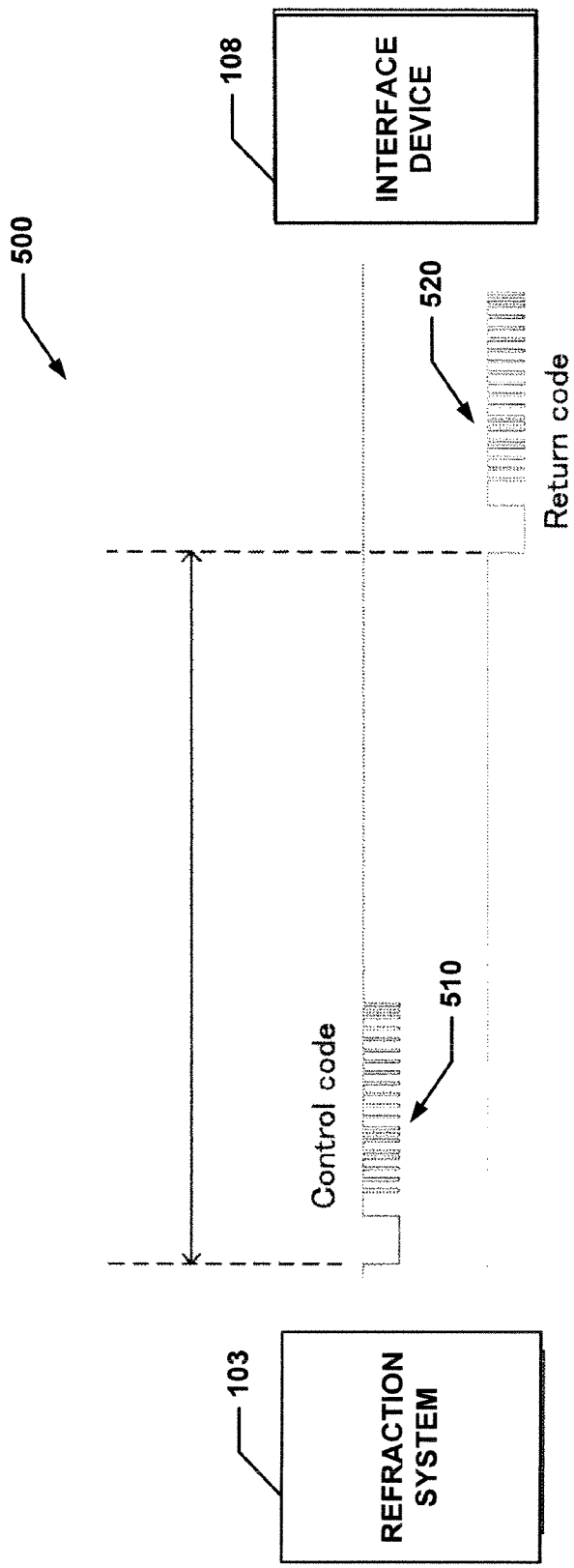
FIG. 5 illustrates a communication sequence between the refraction system and the display, in accordance with an exemplary embodiment.

FIG. 5 illustrates a communication sequence that is emulated by the interface device 108 to facilitate interaction of the refraction system 103 with the display 106. To initiate the communication sequence 500, the refraction system 103 can output a control code. Such control code can be employed to change or modify one or more images that are presented to a subject via the display 106. The interface device 108 receives the control code 510 and responds by sending a return code 520 (e.g., 0x0) within a predetermined window of time if the control code 510 is properly received. If the incorrect code is received, however, the interface device 108 can send a hexadecimal value return code (e.g., 0xF) to the refraction system 103.

In one example, the return code must be sent within a window of time between 60 to 160 milliseconds of receiving the initial control code from the refraction system 103. If a particular return code is sent to the refraction system 103 from the interface device 108, an error can be displayed to the user. In turn, the refraction system 103 can resend the control code if the return code is not received within a predetermined window of time. Control code resending greater than a preset amount (e.g., 15 instances) can cause an error in the refraction system 103. In this manner, the interface device 108 emulates the communication protocol utilized between the refraction system 103 and the display 106.

In one example, the control code 510 includes a header, a refraction system code, a chart code, and a channel code. The header can be utilized to indicate the beginning of the transmission of the control code. Once the header is sent, the refraction system code can be a preset bit length to indicate the model of refraction system utilized for communication. The chart code can be sent after the header and the refraction system code to indicate the type of images to present on the display 106. The channel code corresponds to one of a plurality of channels that can be utilized for communication across a particular cable. It is to be appreciated, however, that substantially any chart model can be accommodated wherein an interface device can receive such chart code commands and convert them for presentation via a display.

In one example, the return code 520 is sent by the interface device 108 to emulate a display. The return code 520 can be employed to verify successful communication has been received from the refraction system 103. The return code 520 can include a header, a refraction system code, a return code, and a channel code. The return code can have a preconfigured header to indicate the beginning of transmission of the return code. The refraction system code can be transmitted to indicate the model of refraction system utilized in the particular configuration. The channel code can be used to identify the channel utilized for communication between the refraction system 103 and the interface device 108.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. An automated ophthalmic system that is utilized to examine the eyes of a subject, comprising:
    a display that presents one or more of an optotype, a chart, a test, and a function to the subject;
    a refraction system that measures a refractive error of at least one eye and identifies a lens to correct the refractive error; and
    an interface device that receives a signal from the refraction system, converts the signal into one or more ASCII characters, and communicates the one or more ASCII characters to the display to present the one or more of an optotype, a chart, a test and a function.

2. The system of claim 1, wherein the refraction system includes an autophoroptor.

3. The system of claim 1, wherein the refraction system communicates with the interface device and the interface device communicates to the display via a serial protocol.

4. The system of claim 1 wherein the optotype presented is one or more of a letter, a number, a tumbling E, a Landolt C, a pictogram, an ETDRS chart, a dot, and a grid.

5. The system of claim 1 wherein the interface device includes a voltage detector that determines if a predefined voltage change is detected from the signal from the refraction system.

6. The system of claim 5, wherein the interface device further includes an ASCII converter that converts the voltage change detected by the voltage detector into one or more hexadecimal codes, the one or more hexadecimal codes are converted into one or more ASCII codes that are output to the display.

7. The system of claim 6, wherein the interface device further includes a lookup table that associates at least one voltage change to at least one ASCII symbol for consumption via the display.

8. A method to facilitate communication between a refraction system and a display within an automated ophthalmic system, comprising:
    connecting an interface device between the refraction system and the display;
    sending a communication from the refraction system to the interface device;
    determining if a predefined voltage change is received within the communication;
    if a predefined voltage change is received, validating the voltage change and sending a response to the refraction system;
    converting the predefined voltage change to an ASCII character; and,
    sending the ASCII character to the display.

9. The method of claim 8, further including detecting whether the response was sent to the refraction system within a predetermined time period.

10. The method of claim 9, further including displaying an error message via the refraction system if the communication sent from the refraction system to the interface device exceeds a predefined value.

11. The method of claim 10, further including presenting one or more of an optotype, a chart, a test and/or a function associated with the ASCII character via the display.

12. The method of claim 11 further including:
initializing ophthalmic software on the display;
sending an ASCII character to a first serial port on the display;
receiving the ASCII character at the interface device via the serial port; and,
returning a character string from the interface device to establish communication between the interface device and the display.

13. An interface device that is utilized to communicate data between a refraction system and a display within an automated ophthalmic system, comprising:
a first data port that receives a voltage signal from the refraction system;
a second data port that facilitates communication between the display and the interface device;
a voltage detector that detects a predefined voltage change from the voltage signal received by the first data port;
an ASCII converter that associates one or more ASCII characters with the voltage change detected by the voltage detector; and
an I/O controller that communicates the one or more ASCII characters from the interface device to the display via the second data port.

14. The device of claim 13, wherein the interface device further includes a memory that contains a lookup table to associate one or more predefined voltage changes with one or more ASCII characters.

15. The device of claim 13, wherein the ASCII character is associated with an optotype, a chart, a test and/or a function.

16. The device of claim 13, wherein the ASCII character is associated with a particular chart, the chart contains a plurality of optotypes.

17. The device of claim 13, wherein the interface device sends or receives data via a wireless protocol.

18. The device of claim 13, wherein the ASCII character is associated with at least one of a positive image of the display, a negative image of the display, a contrast of images presented on the display, and a color of the display.

19. The device of claim 13 wherein the voltage signal from the refraction system is transmitted via a control code, the control code includes a header to indicate the beginning of transmission of the control code;
a refraction system code to identify the refraction system model type utilized for communication;
a chart code to indicate the type of images to present on the display; and,
a channel code to identify a channel that is utilized to communicate the control code.

20. The device of claim 19 wherein the interface device responds to a voltage signal from the refraction system via return code, the return code includes
a header to indicate the beginning of transmission of the return code;
a refraction system code to identify the refraction system model type utilized for communication;
a return code that contains a first character if communication is successful and a second character if communication is unsuccessful; and,
a channel code to identify a channel that is utilized to communicate the control code.

* * * * *